US011020392B2

(12) United States Patent
Yu (10) Patent No.: US 11,020,392 B2
(45) Date of Patent: *Jun. 1, 2021

(54) USE OF TRIMETAZIDINE AS A HEPATOPROTECTIVE MEDICINE IN PREVENTION AND TREATMENT OF LIVER DISEASES AND CONDITIONS

(71) Applicant: Martin Pharmaceuticals, Inc., New York, NY (US)

(72) Inventor: Zujiang Yu, Zhengzhou (CN)

(73) Assignee: Martin Pharmaceuticals, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/240,677

(22) Filed: Aug. 18, 2016

(65) Prior Publication Data

US 2016/0354366 A1 Dec. 8, 2016

Related U.S. Application Data

(63) Continuation-in-part of application No. PCT/CN2016/080219, filed on Apr. 26, 2016.

(30) Foreign Application Priority Data

Apr. 28, 2015 (CN) .......................... 201510207528.0

(51) Int. Cl.
*A61K 31/495* (2006.01)
*A61K 9/00* (2006.01)
*A61K 31/4965* (2006.01)
*A61P 1/16* (2006.01)

(52) U.S. Cl.
CPC ........ *A61K 31/4965* (2013.01); *A61K 9/0019* (2013.01); *A61K 9/0053* (2013.01); *A61K 31/495* (2013.01); *A61P 1/16* (2018.01)

(58) Field of Classification Search
CPC .................................................. A61K 31/4965
USPC .................................................... 514/252.12
See application file for complete search history.

(56) References Cited

U.S. PATENT DOCUMENTS

2006/0205727 A1* 9/2006 Kaesemeyer .......... A61K 31/22
514/237.5

FOREIGN PATENT DOCUMENTS

| CN | WO2010124520 A1 | 11/2010 |
| CN | 102058888 A | 5/2011 |
| CN | 104840462 A | 8/2015 |

OTHER PUBLICATIONS

Archives of Trauma Research. Aug. 2013; 2(2): 63-70, Papadopoulos et al.*
English translation of CN 105287564, Yu (2016).*
Abdel-Salam et al., EXCLI Journal 2011 ;10:162-172.*
Popescu et al. J of Hepatology, V.46, Supplemental 1, S283, published Apr. 2007 (disclosed in IDS by Applicants).*
Fragasso et al. J of the American College of Cardiology, (2006) 48(5) p. 992-998.*
Boissel et al., European Heart Journal (2000), V21, p. 1537-46.*
Nava et al. Therapeiutic and Clinical Risk Management, (2014), V.10, p. 295-303.*
Bhala et al. Hepatology, (2011), 54(4), p. 1208-1216.*
Axley et al. Liver Transplantation, (2019), v.25, p. 695-705.*
Addel-Salam et al. Excli Journal, (2011), v.10, p. 162-172.*
Sarin et al. Hepatol Int. (2009), v.3, p. 269-282.*
Hernaez et al., "Acute-on-chronic liver failure: an update", Gut, (2017); 66, 541-553.*
Mosbah, et al.; "Trimetazidine: Is it a promising drug for use in steatotic grafts?"; World Journal of Gastroeneterology, 12(6): 908-914 (Feb. 2006).
Elimadi, et al.; "Trimetazidine Counteracts the Hepatic Injury Associated with Ischemia-Reperfusion by Preserving Mitochondrial Functions"; The Journal of Pharmacology and Experimental Therapeutics, 286(1): 23-28 (Jul. 1998).
PCT International Search Report issued in application No. PCT/CN2016/080219 dated Aug. 1, 2016.
Abu-Amara et al., "Systematic review of randomized controlled trials of pharmacological interventions to reduce ischaemia-reperfusion injury in elective liver resection with vascular occlusion," International Hepato-Pancreato-Billiary Association, vol. 12, 2010, pp. 4-14.
Borra, Ronald, "Nonalcoholic Fatty Liver Disease in Obesity and Type 2 Diabetes," Dissertation, University of Turku, 2009, 92 pages.

(Continued)

*Primary Examiner* — Yong L Chu
(74) *Attorney, Agent, or Firm* — Thomas W. MacAllister (57) ABSTRACT

This present invention discloses a new use of trimetazidine as a hepatoprotective drug in prevention and treatment of liver diseases, wherein trimetazidine is capable of inhibiting activation of resting T lymphocytes to activated lymphocytes, reducing release of cytokines, and reducing the hepatocyte injury caused by the immune system; capable of inhibiting fatty acid metabolism in hepatocytes and optimizing energy process in hepatocytes; and capable of maintaining normal function of mitochondrial permeability transition pores and reducing hepatocyte apoptosis. Clinical research and trial results suggest that, when administered to patients suffering from liver diseases and conditions, trimetazidine is capable of providing significant hepatoprotective function, and effectively decreasing transaminase levels (including alanine aminotransferase, aspartate transaminase, etc.), with such features as shortening the course of disease, reducing the mortality rate, easy and safe use, and low treatment cost. Trimetazidine is eliminated unchanged mainly through urine, with the elimination half-life of approximately 6 hours, and without hepatic metabolism. Therefore, trimetazidine has minimal liver toxicity, while having significant hepatoprotective effect.

19 Claims, 9 Drawing Sheets

(56) References Cited

OTHER PUBLICATIONS

Girgin et al., "Cytoprotective effects of trimetazidine in carmustine cholestasis," Urban & Fischer, vol. 51, 1999, pp. 326-329.
Kaya et al., "The Effect of Trimetazidine on Liver Regeneration after Partial Hepatectomy under Hepatic Blood Inflow Occlusion," Hepato-Gastroenterology, vol. 50, 2003, pp. 651-655.
Mate et al., "Role of trimetazidine in carbon tetrachloride induced liver damage in rats," International Journal of Basic & Clinical Pharmacology, vol. 3, 2014, pp. 164-170.
Pandey et al., "Perioperative ischaemia-induced liver injury and protection strategies: An expanding horizon for anaesthesiologists," Indian Journal of Anaesthesia, vol. 57, Issue 3, 2013, pp. 223-229.
Popescu et al., "A New Approach in the Treatment of Patients with Nash—Results of a Pilot Study," Alcoholic Liver Disease, NAFLD and Drug-Induced Liver Disease, p. S283, 2007, abstract only.
Settaf et al., "Trimetazidine Ameliorates the Hepatic Injury Associated with Ischaemia-Reperfusion in Rats," Pharmacological Research, vol. 39, No. 3, 1999, pp. 211-216.
Settaf et al., "Trimetazidine prevents ischemia-reperfusion injury in hepatic surgery under vascular clamping," Therapie, vol. 56, No. 5, 2001, pp. 569-574.
Tsimoyiannis et al., "Trimetazine for prevention of hepatic injury induced by ischaemia and reperfusion in rats," The European Journal of Surgery, vol. 159, 1993, pp. 89-93.
Asrani, et al., "Acute-on-Chronic Liver Failure," Clinical Liver Disease, Aug. 2014, 18(3): 561-574 (Author manuscript).
DeMarco, "Trimetazidine: The Heart Drug You've Never Heard Of," Life Extension Magazine, Apr. 2012, at https://www.lifeextension.com/magazine/2012/4/Trimetazidine-Heart-Drug-Never-Heard-Of/Page-01.
Hernaez, et al., "Acute-on-chronic liver failure: an update," Gut, Jan. 2017, vol. 0, pp. 1-13, doi:10.1136/gutjnl-2016-312670.
Jalan, et al., "Acute-on chronic liver failure," Journal of Hepatology, 2017, vol. 57, pp. 1336-1348.
Kamath, "Acute on Chronic Liver Failure," Clinical Liver Disease, Apr. 2017, vol. 9, pp. 86-88.
Kim and Kim, "Acute-on-chronic liver failure," Clinical and Molecular Hepatology 2013, vol. 19, pp. 349-359.
Moreau, et al., "Acute-on-Chronic Liver Failure Is a Distinct Syndrome That Develops in Patients With Acute Decompensation of Cirrhosis," Gastroenterology 2013, vol. 144, pp. 1426-1437.
Peverill, et al., "Evolving Concepts in the Pathogenesis of NASH: Beyond Steatosis and Inflammation," International Journal of Molecular Sciences, 2014, vol. 15, pp. 8591-8638; doi:10.3390/ijms15058591.
Shi, et al.: "Human Mesenchymal Stem Cell Transfusion Is Safe and Improves Liver Function in Acute-on-Chronic Liver Failure Patients," Stem Cells Translational Medicine, Oct. 11, 2012, vol. 1, pp. 725-731.
Simonetto et al., "Improving survival in ACLF: growing evidence for use of G-CSF," Hepatology International, 2017, vol. 11, pp. 473-475.
European Medicines Agency, "European Medicines Agency recommends restricting use of trimetazidine-containing medicines," Jun. 22, 2012, https://www.ema.europa.eu/en/news/european-medicines-agency-recommends-restricting-use-trimetazidine-containing-medicines.
The National Institute of Diabetes and Digestive and Kidney Diseases Health Information Center, "Treatment for NAFLD & NASH, How do doctors treat NAFLD and NASH?," Nov. 2016, https://www.niddk.nih.gov/health-information/liver-disease/nafld-nash/treatment.
European Patent Office, Communication, dated Oct. 10, 2018.
EPO Machine Translation of WO2010/124520 A1.

\* cited by examiner

USE OF TRIMETAZIDINE AS A HEPATOPROTECTIVE MEDICINE IN PREVENTION AND TREATMENT OF LIVER DISEASES AND CONDITIONS

CROSS-REFERENCE TO RELATED APPLICATIONS

This application is a continuation-in-part of International Patent Application No. PCT/CN2016/080219 filed Apr. 26, 2016, which claims the benefit of Chinese Patent Application No. 2015-10207528 filed Apr. 28, 2015, the contents of both of which are incorporated herein by reference in their entireties.

TECHNICAL FIELD

The present invention relates to a novel use of trimetazidine (TMZ) as a hepatoprotective medicine in prevention and treatment of liver diseases and conditions.

BACKGROUND

Trimetazidine hydrochloride (1-[2,3,4-trimethoxybenzyl] piperazine dihydrochloride) has been used mainly in prevention and treatment of angina pectoris. It is a miscellaneous class cardiovascular drug against angina pectoris, wherein TMZ prevents the ATP level in cells from decreasing by maintaining proper energy metabolism of cells in a hypoxic or ischemic state, thereby guaranteeing normal functioning of the ion pump and normal operation of the transmembrane sodium-potassium flow and maintaining a stable internal environment of cells. Therefore, it is an effective drug against myocardial ischemia.

Hepatoprotective drugs refer to the category of drugs used to protect liver functions, characterized in that they are capable of maintaining liver functions, reducing hepatocyte injury, promoting repair and regeneration of injured hepatocyte, and enhancing the detoxifying function of the liver. At present, there is a shortage of large-scale evidence-based medicine and action target researches on hepatoprotective drugs. It is known that current hepatoprotective drugs mainly include the detoxifying category (reductive glutathione, tiopronin, etc.), the hepatocyte regeneration promoting category (hepatocyte growth-promoting factor, polyene phosphatidylcholine), the energy metabolism promoting category (water-soluble vitamins, coenzymes, potassium aspartate magnesium, ornithine aspartate), the cholagogue category (ademetionine, methionine and Vitamin B1, anethol trithione), and the anti-inflammatory traditional Chinese medicine (silibin, compound glycyrrizin preparation). The effect of hepatoprotective drugs are relative. Most drugs, including most hepatoprotective drugs, are metabolized in the liver, which increases the liver's burden of detoxification and metabolism.

Although there are a great variety of existing hepatoprotective drugs, they have either single or unidentified action target and relatively limited "hepatoprotective" effects. Since most drugs, not excluding most hepatoprotective drugs, are metabolized in the liver, it increases the burden of the liver, which is particularly problematic in patients suffering from liver failure. Most patients suffering from chronic liver diseases and some suffering from acute liver diseases die of the end stage liver failure. For example, all liver diseases caused by virus, drugs, alcohol, non-alcoholic fatty liver or autoimmunity or genetic and metabolic liver diseases can result in liver failure. In recent years, liver failure is treated mainly through combined treatment, by preventing and treating all sorts of clinical complications, delaying hepatocyte damage and waiting for hepatocyte regeneration. Currently there is no effective drug to treat liver damage and liver failure induced by various liver diseases.

SUMMARY

In order to overcome the deficiencies of existing therapeutic options, the present invention discloses a novel use of trimetazidine as a hepatoprotective drug in prevention and treatment of liver diseases and conditions, with significant hepatoprotective effect in treating liver damage induced by virus, drugs, autoimmunity, non-alcoholic fatty liver and many other causes.

Accordingly, disclosed here is a method for treating a liver disease or condition, comprising administrating to a subject in need thereof a pharmaceutical composition comprising an effective amount of trimetazidine or a pharmaceutically acceptable salt thereof as an active ingredient.

In some embodiments, the pharmaceutical composition is orally administered to the subject. In some embodiments, the pharmaceutical composition is parentally administered to the subject.

In some embodiments, the pharmaceutical composition is administered to the subject 1-4 times daily. In some embodiments, the pharmaceutical composition is administered to the subject 2 or 3 times daily. In some embodiments, the pharmaceutical composition is administered to the subject 1 time daily.

In some embodiments, the subject is administered with about 30-180 mg daily of trimetazidine or a pharmaceutically acceptable salt thereof. In some embodiments, the subject is administered with about 60 mg daily of trimetazidine or a pharmaceutically acceptable salt thereof.

In some embodiments, the active ingredient of the pharmaceutically composition consists essentially of trimetazidine or a pharmaceutically acceptable salt thereof. In some embodiments, the active ingredient of the pharmaceutically composition consists of trimetazidine or a pharmaceutically acceptable salt thereof.

In some embodiments, the pharmaceutically composition further comprises a pharmaceutically acceptable carrier.

In some embodiments, the liver disease or condition is hepatitis or cirrhosis. In some embodiments, the liver disease or condition is viral hepatitis, alcoholic hepatitis, autoimmune hepatitis, alcoholic fatty liver disease, or non-alcoholic fatty liver disease.

In some embodiments, the liver disease or condition is liver failure (e.g., chronic liver failure or acute liver failure). In some embodiments, the liver disease or condition in absence of treatment develops into acute liver failure in about a month, about a week, or about 72 hours.

In some embodiments, the subject is not suffering from angina pectoris, coronary insufficiency, old myocardial infarction, coronary heart disease, vertigo or tinnitus.

In some embodiments, the pharmaceutically composition reduces activation of resting T lymphocytes to activated lymphocytes in the subject.

In some embodiments, the pharmaceutically composition reduces fatty acid metabolism in hepatocytes and promotes aerobic oxidation of glucose in the subject.

In some embodiments, the pharmaceutically composition reduces β-oxidation in hepatocytes and reduces formation of ROS in the subject.

In some embodiments, the subject before treatment has a blood alanine aminotransferase (ALT) level of at least 200 U/L, or at least 300 U/L, or at least 400 U/L, or at least 500 U/L, or up to 1500 U/L, or up to 1000 U/L, or up to 600 U/L, or up to 400 U/L.

In some embodiments, the pharmaceutically composition reduces blood ALT level in the subject by at least 100 U/L, or at least 150 U/L, or at least 200 U/L, or at least 250 U/L, or at least 300 U/L after 15 days of treatment. In some embodiments, the pharmaceutically composition reduces blood ALT level in the subject by at least 100 U/L, or at least 150 U/L, or at least 200 U/L, or at least 250 U/L, or at least 300 U/L after 5 days of treatment. In some embodiments, the pharmaceutically composition reduces blood ALT level in the subject by at least 20%, or at least 30%, or at least 50%, or at least 70% after 15 days of treatment. In some embodiments, the pharmaceutically composition reduces blood ALT level in the subject by at least 20%, or at least 30%, or at least 50%, or at least 70% after 5 days of treatment.

In some embodiments, the subject before treatment has a blood aspartate transaminase (AST) level of at least 200 U/L, or at least 300 U/L, or at least 400 U/L, or at least 500 U/L, or up to 1500 U/L, or up to 1000 U/L, or up to 600 U/L, or up to 400 U/L.

In some embodiments, the pharmaceutically composition reduces blood AST level in the subject by at least 100 U/L, or at least 150 U/L, or at least 200 U/L, or at least 250 U/L, or at least 300 U/L, or at least 400 U/L after 15 days of treatment. In some embodiments, the pharmaceutically composition reduces blood AST level in the subject by at least 100 U/L, or at least 150 U/L, or at least 200 U/L, or at least 250 U/L, or at least 300 U/L, or at least 400 U/L after 5 days of treatment. In some embodiments, the pharmaceutically composition reduces blood AST level in the subject by at least 20%, or at least 30%, or at least 50%, or at least 70%, or at least 80% after 15 days of treatment. In some embodiments, the pharmaceutically composition reduces blood AST level in the subject by at least 20%, or at least 30%, or at least 50%, or at least 70%, or at least 80% after 5 days of treatment.

These and other features, together with the organization and manner of operation thereof, will become apparent from the following detailed description when taken in conjunction with the accompanying drawings.

DETAILED DESCRIPTION

Reference will now be made in detail to some specific embodiments of the invention contemplated by the inventors for carrying out the invention. Certain examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, well known process operations have not been described in detail in order not to unnecessarily obscure the present invention.

Various techniques and mechanisms of the present invention will sometimes be described in singular form for clarity. However, it should be noted that some embodiments include multiple iterations of a technique or multiple instantiations of a mechanism unless noted otherwise.

The invention relates to a novel use of trimetazidine as a hepatoprotective drug in prevention and treatment of liver diseases and conditions including hepatitis, cirrhosis, viral hepatitis, alcoholic hepatitis, autoimmune hepatitis, alcoholic fatty liver disease, non-alcoholic fatty liver disease, and liver failure.

Trimetazidine as a hepatoprotective drug as described herein, wherein trimetazidine is capable of: inhibiting activation of resting T lymphocytes to activated lymphocytes and macrophage, reducing release of cytokines, and reducing hepatocyte injury caused by immune system; inhibiting fatty acid metabolism in hepatocytes and optimizing energy metabolism process in hepatocytes; maintaining normal function of mitochondrial permeability transition pores and reducing hepatocyte apoptosis.

Trimetazidine as a hepatoprotective drug as described herein, wherein in hepatoprotective action, trimetazidine is capable of inhibiting fatty acid metabolism, in particular inhibiting mitochondrial ketoacyl thiolase activity, thereby inhibiting cell fatty acid β-oxidation and reducing ROS reaction; wherein trimetazidine is capable of enhancing mitochondrial pyruvate dehydrogenase activity, thereby promoting aerobic oxidation of glucose which, in ischemic cells, requires lower oxygen consumption than β-oxidation to obtain energy, and wherein trimetazidine is capable of optimizing the energy process in hepatocytes, thereby maintaining proper energy metabolism during ischemia.

Trimetazidine as a hepatoprotective drug as described herein, wherein trimetazidine achieves hepatoprotective effects primarily through the following three aspects:

1. As lymphocyte activation requires ATP provided by fatty acid metabolism, trimetazidine is capable of inhibiting free fatty acid (FFA) metabolism, inhibiting activation of resting T lymphocytes to activated lymphocytes, thereby reducing release of cytokines by activated cytotoxic T lymphocytes, reducing exogenous cell necrosis or apoptosis, and reducing hepatocyte injury caused by human immune system.

2. As hepatocytes during liver failure are under an adverse environment with high ammonia, low oxygen and high bilirubin, have severely affected cellular generation of ATP, which in turn inhibits development and growth of the hepatocytes, trimetazidine is capable of inhibiting fatty acid metabolism in the hepatocytes, promoting glucose glycolysis and subsequent tricarboxylic acid (TCA) cycle, reducing oxygen atoms required for generating the same amount of ATP, and facilitating the use of limited oxygen atoms for oxidizing glucose to provide ATP needed by hepatocytes to synthesize active substances comprising RNA, DNA, and protein; wherein it is common in liver injury, especially during liver failure, that the formation of microthrombus in injured liver leads to a hypoxic state for hepatocytes; and wherein trimetazidine is also capable of inhibiting FFA metabolism, reducing the formation of ROS in hepatocytes, and reducing secondary hepatocyte injury.

3. As hepatocyte injury causes damage to mitochondria, reduces ATP synthesis and natural immunity, which can be characterized by opening of MPT and efflux of K+ and Ca2+, thereby initiating endogenous apoptosis, as particularly shown in hepatocyte injury caused by high blood ammonia, trimetazidine is capable of maintaining proper release of calcium ions by MPT pores and reducing hepatocyte apoptosis.

The present invention provides a therapeutic approach for treating liver diseases, so as to slow or reverse the patient's progression to liver failure. In this context, "liver disease" denotes a condition where liver damage and inflammation threatens to progress to a fatal loss of liver function and/or regenerative capacity. Thus, "liver disease" as used in this description encompasses hepatitis, where inflammation causes damage to liver cells and liver function, whether caused by any virus (viral hepatitis), by a liver toxin (e.g., alcoholic hepatitis), or by autoimmunity (autoimmune hepatitis). Also illustrative of "liver disease" in this description are (A) fatty liver disease (hepatic stetosis), a condition where large vacuoles of triglyceride fat accumulate in liver cells, and (B) non-alcoholic fatty liver disease, which subsumes a spectrum of disease associated with obesity and metabolic syndrome, where either (A) or (B) threatens liver damage so severe as to cause a fatal loss of liver function and/or regenerative capacity.

During a liver disease, damage of the normal liver structure impacts blood supply to the liver. Although up to date, ischemia and hypoxia are not considered as a typical characteristic of liver disease, the inventor discovers that liver injury causes local ischemia and hypoxia of liver. Moreover, another main provoking factor of liver injury is hepatic inflammatory response, resulting in the reduced physiological function and regeneration capacity of the liver. Based on the above pathological characteristics of hypoxia and inflammatory response in a liver disease, the present invention provides a new therapeutic approach for treating liver diseases. The positive and beneficial results: as shown in clinical research and trial results, when administered to patients suffering from liver diseases and conditions, TMZ is capable of providing significant hepatoprotective function, effectively decreasing transaminase levels (including alanine aminotransferase, aspartate transaminase, etc.), with such features as shortening the course of disease, reducing the mortality rate, easy and safe use, and low treatment cost. TMZ is mainly eliminated unchanged by way of urine, with the elimination half-life of approximately 6 hours, and without hepatic metabolism. Therefore, TMZ has minimal liver toxicity, while having significant hepatoprotective effect.

Figure 3:
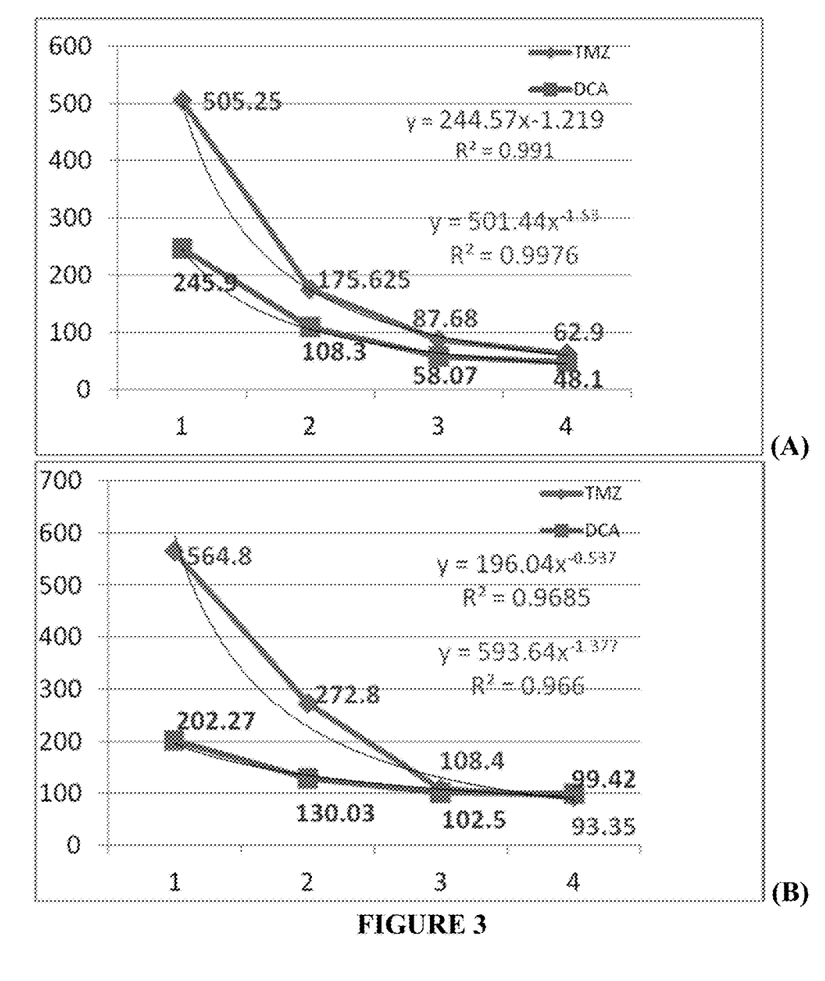
FIG. 3 shows dynamic changes of (A) ALT and (B) AST within 15 days after treatment with TMZ and DCA, respectively. Both TMZ group and DCA group were also administered with LOLA.
Figure 5:
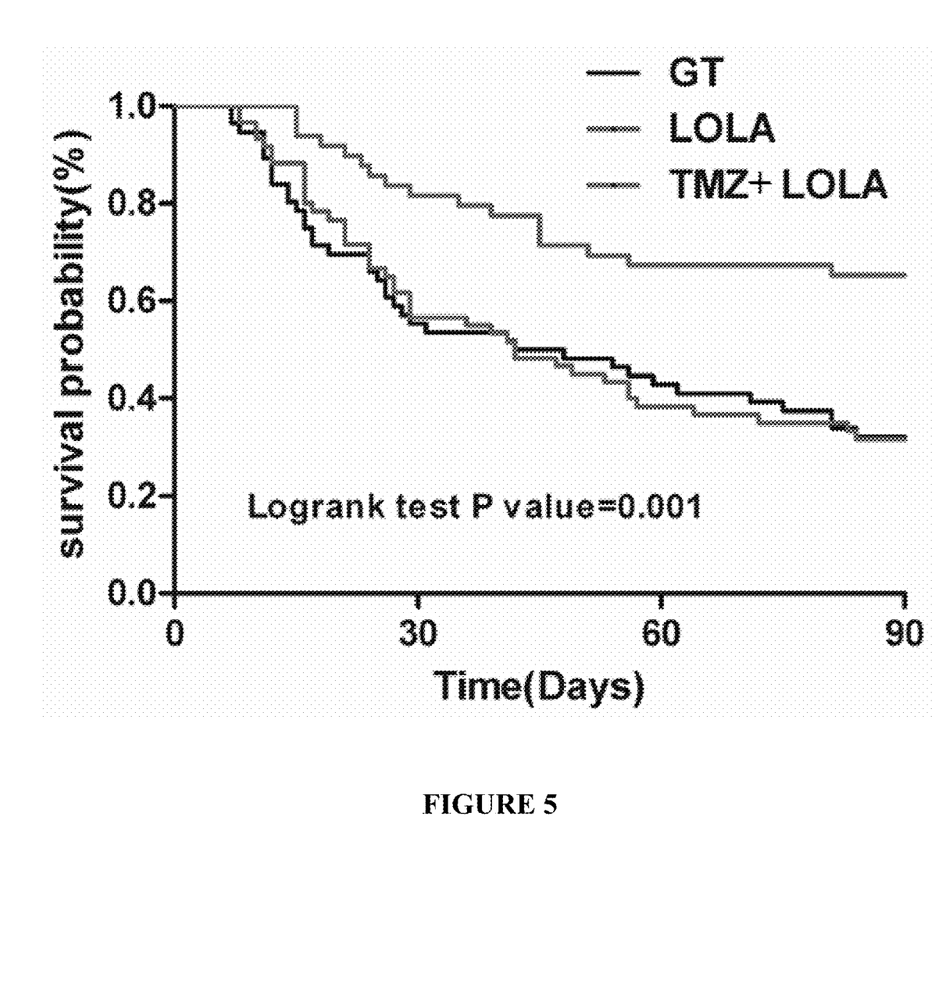
FIG. 5 shows survival curves of liver failure patients treated with general treatment (GT), LOLA, and TMZ+LOLA, respectively.
Figure 6:
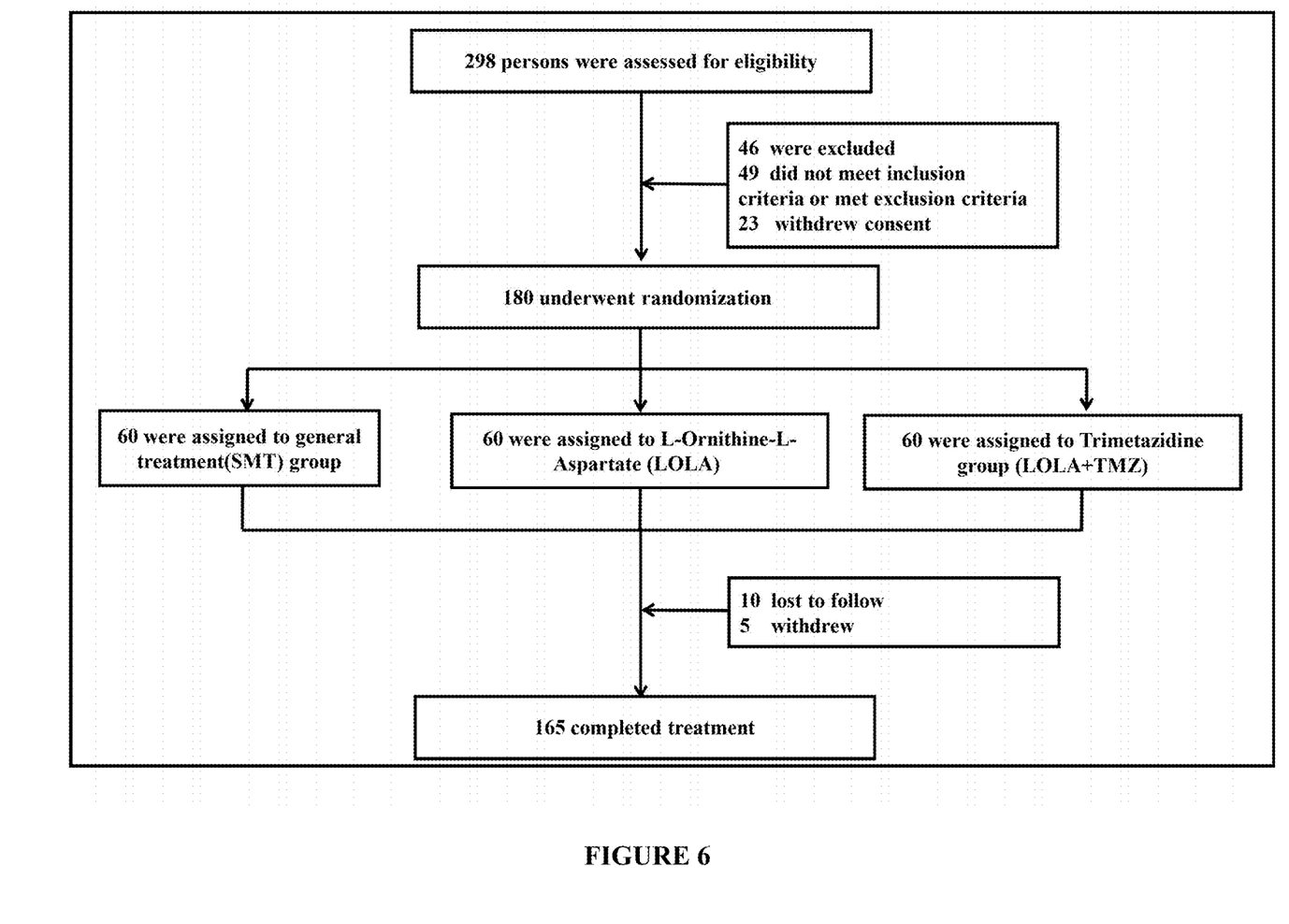
FIG. 6 shows a design flowchart of a TMZ clinical trial involving 165 liver failure patients.

In a clinical trial and research involving 165 cases of liver failure (see FIG. 6), we administered TMZ tablets (20 mg/tablet) orally to the liver failure patients, one tablet each time, three times a day, over a 4-week course of treatment. As shown in the clinical trial result, compared with traditional therapeutic approach, the 30-day immortality rate of liver failure patients in the TMZ treatment group dropped from 44% to approximately 18%, and the 90-day immortality rate from 68% to 35% (see FIG. 5). This suggests that early TMZ intervention in liver failure patients can significantly increase the survival rate and improve their prognosis. Furthermore, the laboratory test indicators suggest that TMZ can significantly raise the decrease rate of alanine aminotransferase and aspartate transaminase (see FIG. 3). One patient received a PET-CT test of the imaging changes of liver, and the result suggests that, after taking TMZ, the hepatic glucose metabolism of the liver failure patient was remarkably improved (see FIG. 4). This clinical trial result suggests that early use of TMZ for liver failure patients can significantly improve their liver function, inhibit hepatic inflammatory response, enhance their hepatic glucose metabolism and energy utilization, and improve their chances of survival.

With respect of drug safety, as TMZ is mainly eliminated unchanged through urine, with an elimination half-life of 6 hours and without hepatic metabolism, it causes minimal liver toxicity, and no serious adverse reaction occurred during the clinical trial, with high patient tolerability and high safety.

Carriers, excipients and other additives commonly used for pharmaceutical preparations may be used to prepare pharmaceutical compositions comprising trimetazidine or pharmaceutically acceptable salts thereof as active ingredients.

The administration forms may be oral dosage forms, such as tablets, pills, capsules, granules, powders, emulsions, syrups, suspensions, liquid preparations, or non-oral dosage forms, such as intravenous injection or intramuscular injection, suppository, subcutaneous agent, transdermal agent, nasal agent, inhalation. Symptoms, age, gender, etc. of the individual patient should be considered in order to properly determine the dose of a compound. Generally speaking, in the case of oral administration, daily dosage for adult patients of the compound is about 0.001 mg/kg to 100 mg/kg, a single dose or divided into 2 to 4 times daily. In the case of intravenous administration according to the patient symptoms, generally speaking, daily dose for adult patients is 0.0001 mg/kg to 10 mg/kg, once to more times daily. Further, in the case of using the inhalant administration, generally speaking, daily dosage for adult patients is 0.0001 mg/kg to 1 mg/kg, once to more times daily.

In some embodiments, an adult patient may take orally a pharmaceutical composition comprising about 30-180 mg trimetazidine or a pharmaceutically acceptable salt thereof as an active ingredient daily, in a single dose or 2 to 4 separate doses, with each dose comprising about 10-60 mg trimetazidine. In some embodiments, an adult patient may take orally a pharmaceutical composition comprising about 60 mg trimetazidine or a pharmaceutically acceptable salt thereof as an active ingredient daily, in 3 separate doses, with each dose comprising about 20 mg trimetazidine.

In the present invention, solid compositions for oral administration may be tablets, powders, granules and the like. In such solid compositions, one or more active substances are mixed with at least one inert excipient (e.g., lactose, mannitol, glucose, hydroxypropylcellulose, microcrystalline cellulose, starch, polyvinyl pyrrolidone, magnesium aluminum silicate, etc.). According to a conventional method, the composition may also contain inert additives such as lubricants (e.g. magnesium stearate), disintegrating agents (e.g., sodium carboxymethyl starch) and dissolution aids. If necessary, tablets or pills may be coated with sugar coating or a gastric or enteric coating agent.

The liquid compositions for oral administration include pharmaceutically acceptable emulsions, solutions, suspensions, syrups, elixirs, and commonly used inert diluent (e.g., purified water, ethanol). In addition to the inert diluent, the composition may also contain additives such as solubilizing agents, wetting agents and suspending agents, as well as sweetener, flavoring agents and preservatives.

Injections for non-oral administration include sterile aqueous or non-aqueous liquid preparations, suspensions and emulsions. Diluent for aqueous solution can include (for example) distilled water for injection and physiological saline. Diluent for non-aqueous solution can include (e.g.) propylene glycol, polyethylene glycol, vegetable oils (such as olive oil), alcohols (e.g. ethanol) and polysorbate 80. Such compositions may further contain isotonic agents, preservatives, wetting agents, emulsifying agents, dispersing agents, stabilizing agents, dissolving aids and the like additives. Such compositions may be sterilized by filtration through a bacteria retaining filter, adding bactericides or irradiation with light. In addition, these compositions may be made into sterile solid compositions, and then dissolved or suspended, prior to use, with sterile water or a sterile solvent for injection.

Transmucosal agents, such as inhalations and nasal agents and the like, can be solid, liquid, or semi-solid state of use, and can be prepared in accordance with conventionally known methods. For example, an excipient (e.g., lactose and starch), pH adjusting agent, a preservative, surfactants, lubricants, stabilizing agents, thickening agents and the like may be added as needed. You can use a suitable inhalation or insufflation device for administration. For example, a metered dose inhaler or other conventionally known devices or sprayers may be used to administer the compound alone or as a powder mixture after power formulation. In addition, the compound may also be combined with a pharmaceutically acceptable carrier, and administered as a solution or suspension. The dry powder inhaler or the like may be used for a single dose or multiple doses, and can use a dry powder or a powder-containing capsule. Further, a pressurized aerosol spray and the like can also be used for administration by the use of a suitable propellant (e.g., chlorofluoroalkane, hydrofluoroalkane, or a suitable gas such as carbon dioxide).

ADDITIONAL EMBODIMENTS

Embodiment 1

A method for treating a liver disease or condition, comprising administrating to a patient in need thereof a pharmaceutical composition comprising trimetazidine or a pharmaceutically acceptable salt thereof as an active ingredient.

Embodiment 2

A method for treating hepatitis, comprising administrating to a patient in need thereof a pharmaceutical composition comprising trimetazidine or a pharmaceutically acceptable salt thereof as an active ingredient.

Embodiment 3

A method for treating cirrhosis, comprising administrating to a patient in need thereof a pharmaceutical composition comprising trimetazidine or a pharmaceutically acceptable salt thereof as an active ingredient.

Embodiment 4

A method for treating liver failure, comprising administrating to a patient in need thereof a pharmaceutical composition comprising trimetazidine or a pharmaceutically acceptable salt thereof as an active ingredient.

Embodiment 5

A method for treating viral hepatitis, comprising administrating to a patient in need thereof a pharmaceutical composition comprising trimetazidine or a pharmaceutically acceptable salt thereof as an active ingredient.

Embodiment 6

A method for treating alcoholic hepatitis, comprising administrating to a patient in need thereof a pharmaceutical composition comprising trimetazidine or a pharmaceutically acceptable salt thereof as an active ingredient.

Embodiment 7

A method for treating autoimmune hepatitis, comprising administrating to a patient in need thereof a pharmaceutical composition comprising trimetazidine or a pharmaceutically acceptable salt thereof as an active ingredient.

Embodiment 8

A method for treating alcoholic fatty liver disease or non-alcoholic fatty liver disease, comprising administrating to a patient in need thereof a pharmaceutical composition comprising trimetazidine or a pharmaceutically acceptable salt thereof as an active ingredient.

Embodiment 9

A method for inhibiting activation of resting T lymphocytes to activated lymphocytes in liver disease patients, comprising administrating to a patient in need thereof a pharmaceutical composition comprising trimetazidine or a pharmaceutically acceptable salt thereof as an active ingredient.

Embodiment 10

A method for inhibiting fatty acid metabolism in hepatocytes and promoting aerobic oxidation of glucose in liver disease patients, comprising administrating to a patient in need thereof a pharmaceutical composition comprising trimetazidine or a pharmaceutically acceptable salt thereof as an active ingredient.

Embodiment 11

A method for inhibiting β-oxidation in hepatocytes and reducing formation of ROS in liver disease patients, comprising administrating to a patient in need thereof a pharmaceutical composition comprising trimetazidine or a pharmaceutically acceptable salt thereof as an active ingredient.

Embodiment 12

A method for reducing alanine aminotransferase (ALT) and/or aspartate transaminase (AST) in liver disease patients, comprising administrating to a patient in need thereof a pharmaceutical composition comprising trimetazidine or a pharmaceutically acceptable salt thereof as an active ingredient.

Embodiment 13

The method of any of Embodiments 1 to 12, comprising administering trimetazidine to the patient orally or by injection.

Embodiment 14

The method of any of Embodiments 1 to 13, comprising administering 30-180 mg trimetazidine to the patient daily.

Embodiment 15

The method of any of Embodiments 1 to 14, comprising administering 60 mg trimetazidine to the patient daily.

Embodiment 16

The method of any of Embodiments 1 to 15, comprising administering trimetazidine to the patient 1-4 times daily.

Embodiment 17

The method of any of Embodiments 1 to 16, comprising administering trimetazidine to the patient 3 times daily.

Embodiment 18

The method of any of Embodiments 1 to 17, wherein the pharmaceutical composition administered to the patient contains trimetazidine or a pharmaceutically acceptable salt thereof as the sole active ingredient.

Embodiment 19

The method of any of Embodiments 1 to 18, wherein the liver disease or condition in absence of treatment develops into acute liver failure in a month, a week, or 72 hours.

Embodiment 20

The method of any of Embodiments 1 to 19, wherein the patient is not suffering from angina pectoris, coronary insufficiency, previous myocardial infarction, coronary heart disease, vertigo or tinnitus.

WORKING EXAMPLES

Example 1—Clinical Research on the Hepatoprotective Effect of Trimetazidine in Hepatic Failure Patients I. Objective of Trial
Evaluate if trimetazidine is capable of improving the liver function of patients with hepatic failure.
II. Design of Trial
1. Trial Method
The single-center cohort study was adopted as the clinical trial method.
2. Estimation and Distribution of the Number of Cases
In accordance with relevant references and the results of previous trials, the number of cases shall be no less than 50. Taking into account the number of loss to follow up and possible drop-out (to be controlled around 10%), 60 cases are required to be selected (30 cases for the trial group and 30 cases for the control group). Now the First Affiliated Hospital of Zhengzhou University has completed the clinical observation of 58 cases.
3. Cohort Groups
All serious hepatitis patients enrolled between Aug. 19, 2014 and Dec. 19, 2014 were put in the control group; and all those enrolled between December 9 and the application date were in the trial group.
III. Selection of Cases
1. Selection Criteria
Patients diagnosed with liver failure complicated by myocardial damage (conforming to the diagnosis criteria as specified in the 2012 edition of A Guide to Diagnosis and Treatment of Liver Failure, promulgated by the Society of Infectious Diseases under Chinese Medical Association and the Society of Hepatology under CMA: suffering from hepatic encephalopathy; extremely feeble, with significant alimentary canal symptoms; with icterus deepening fast, and serum TBIL 10 times higher than the normal upper limit or increasing by ≥17.1 umol/l daily; with PTA≤40% or INR≥1.5, exclusive of other causes; ascites decompensation)
Age: 18~70;
Male or female;
Inpatient;
Patients signing the informed consent, with good compliance.
2. Exclusion Criteria
Patients under 18 or over 70 years old;
Patients diagnosed with shock liver (ischemic liver disease);

Patients with liver failure in pregnancy or HELLP syndrome;

Patients with liver failure secondary to malignant tumor in the liver;

Patients with refractory hypotension

Patients with septic shock;

Patients about to receive liver transplant (within 8 hours);

Patients allergic to trimetazidine drug;

Patients tolerant of trimetazidine drug;

Abuser of drugs and/or alcohol;

Pregnant or lactation women;

Patients with recent myocardial infarct (within half a year);

Patients with serious renal inadequacy.

3. Dismissal Criteria

Cases nonconforming to the selection criteria or with nonconforming records in the case report;

Cases dropping out of the trial not because of adverse reaction or poor effect.

4. Drop-Out Criteria for Subjects

Researcher considers it necessary to discontinue the trial with the subject from a medical point of view;

Patient requests to stop the trial;

Occurrence of a serious adverse event.

IV. Drugs Used in Trial and Drug Distribution

1. Trial group: trimetazidine (TMZ): 20 mg/tablet, provided by Servier (Tianjin) Pharmaceutical Co. Ltd. Usage and dosage: 1 tablet each time, 3 times daily, oral administration, for a 4-week course of treatment.

2. Control group: Diisopropylamine Dichloroacetate (DCA) (80 mg/D) for the control group in this trial, provided by Dandong Yichuang Pharmaceutical Co., Ltd, for a 4-week course of treatment.

3. Both trial group and control group were also given basic treatment to meet ethical requirements. Basic treatment includes administration of L-ornithine-L-aspartate (LOLA), reductive glutathione, magnesium isoglycyrrhizinate and human serum albumin upon hospital admission. HBV-related liver failure patients were also treated with lamivudine.

V. Test of Liver Function Indicators

1. Alanine aminotransferase (ALT), tested by chromatometry, with products provided by Roche Diagnostics (Shanghai) Ltd.

2. Aspartate transaminase (AST), tested by chromatometry, with products provided by Roche Diagnostics (Shanghai) Ltd.

VI. Analysis of Test Results

Figure 1:
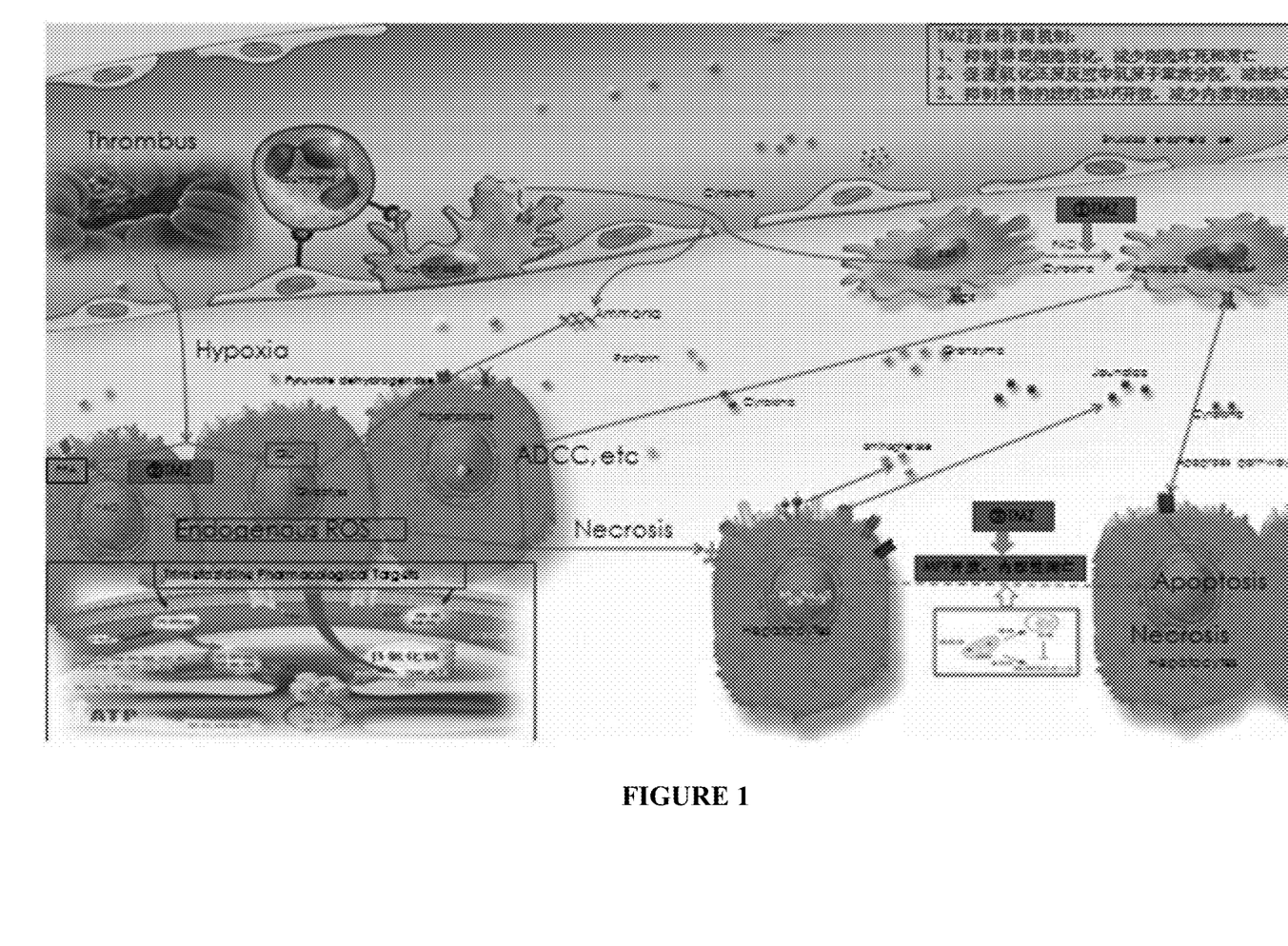
FIG. 1 shows hepatoprotective mechanism of TMZ, which may include (i) inhibiting activation of lymphocytes, thereby reducing cell necrosis or apoptosis; (ii) promoting redistribution of oxygen atoms in oxidation-reduction reactions, thereby reducing ROS; and (iii) inhibiting opening of MPT of damaged mitochondria, thereby reducing endogenous apoptosis.
Figure 2:
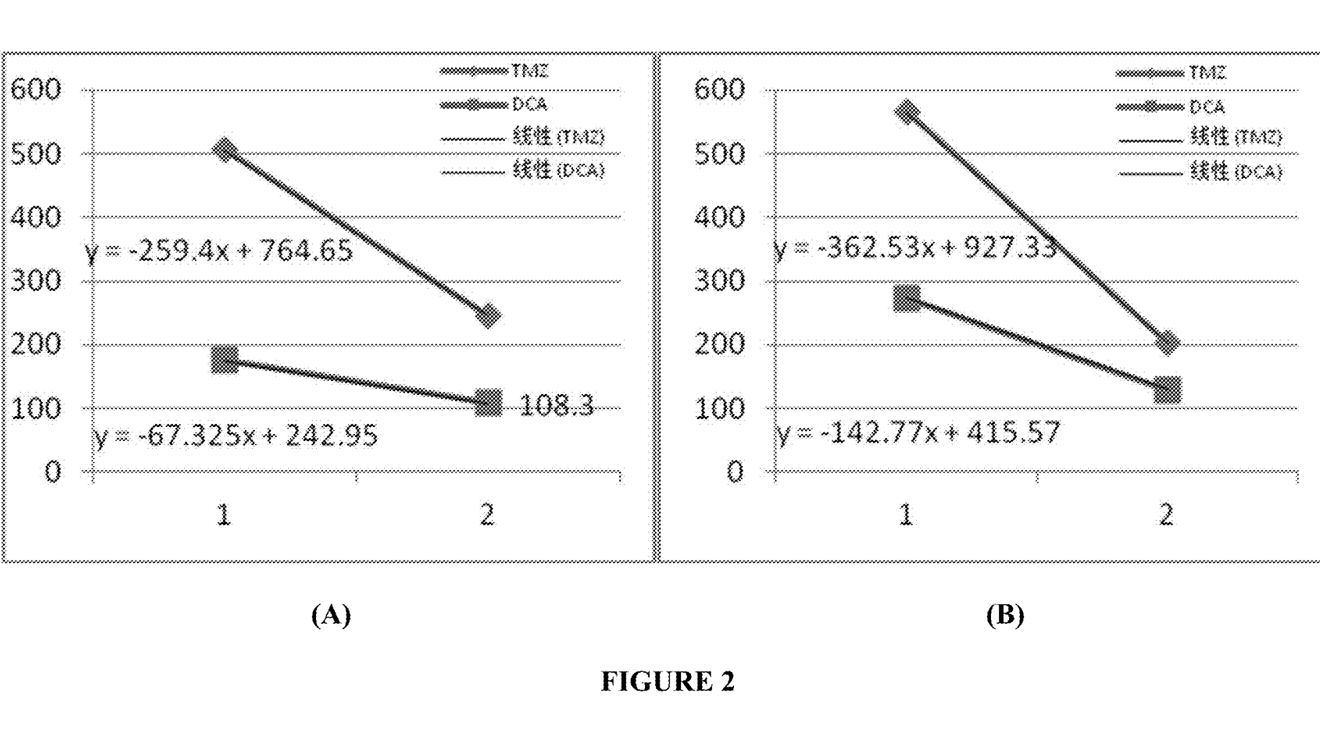
FIG. 2 shows dynamic changes of (A) ALT and (B) AST within 5 days after treatment with TMZ and DCA, respectively. Both TMZ group and DCA group were also administered with LOLA.

1. Maintenance of Liver Function a. After 5 days of treatment, the comparison of ALT and AST decrease in liver failure and relevant mathematical model analysis showed that the ALT decrease of the TMZ group (k=259.4) was much greater than that of the DCA control group (k=67.325); and the AST decrease of the TMZ group (k=362.53) was also much greater than the DCA control group (k=142.77), indicating that TMZ is capable of reducing transaminase to a lower level in a short time, thereby reducing hepatocyte injury. See FIG. 2.

b. Within 15 days of treatment, the comparison of ALT and AST decrease in liver failure and relevant mathematical model analysis showed conformance to the indicators decrease model. The ALT decrease of the TMZ group (y=501.44x−1.53) was much greater than that of the DCA control group (y=244.57x−1.219); and it was more obvious with the AST decrease, where the TMZ group (y=593.64x−1.377) was much greater than the DCA control group (y=196.04x−0.537), indicating that TMZ is capable of reducing higher transaminase to a lower level in the same length of time, thereby reducing hepatocyte injury and, in particular, significantly facilitating maintenance of mitochondrial damage. See FIG. 3.

2. Adverse Event

General adverse reaction event: currently both groups are safe, with only a few adverse events and without any serious adverse event.

3. Kidney Function Damage: the Kidney Function Test Results Showed No Statistical Difference Between the Two Groups.

Conclusion: Trimetazidine is capable of reducing the ALT and AST levels in a short period of time, also efficiently reducing higher ALT and AST levels, and in particular significantly reducing the AST level. Thus, TMZ in comparison with DCA has higher capability of maintaining the liver function and lower toxic and side effects.

VII. Clinical Cases

Case 1: Ms. Lu, female, age 50, had past positive HBsAg for over 20 years, during which she took multiple reexaminations of liver function and, as the results of all color ultrasound examinations were within normal range, she was not given any special treatment. Three months before, after catching cold and overwork, she developed abdominal distension and yellow urine, and was admitted to hospital following aggravation of the condition over 6 days. On admission, she was complicated with massive seroperitoneum and serious xanthochromia throughout the skin and mucosa of her whole body, feeling serious nausea, anorexia and feebleness. Examinations after admission showed ALT 270 u/L, AST 303 u/L and ALB (serum albumin) 19 g/L. At the First Affiliated Hospital of Zhengzhou University, on the basis of combined treatment, TMZ was administered to her three times a day and one tablet each time. 12 days thereafter, the reexamination results showed ALT 41 u/L and AST 68 u/L. Her ascites faded away, with markedly improved energy and appetite. Following consolidation therapy for more than 10 days, she was discharged from hospital, whereafter she continued to take the medicine for 4 weeks, her liver enzyme was fully back to normal and she did not feel feeble or anorexic.

Case 2: Mr. Wang, male, age 51, had had yellow urine for 25 days and dry mouth and bitter taste in mouth for 10 days before he came to the First Affiliated Hospital of Zhengzhou University. The examination upon hospital admission showed ALT 983 u/L, AST 484 u/L and total bilirubin at 401.9 umol/L. After admission, he was examined for viral hepatitis (−) and autoimmune hepatitis (−), and was ruled out hepatic vascular disease and Budd-Chiari syndrome. Detailed inquiry of his medical history revealed that the patient had taken fallopia multiflora tea for more than 3 months, and he was tentatively diagnosed with serious drug-induced hepatitis. On the basis of combined treatment of liver protection and jaundice removing, oral administration of TMZ was added for 20 days, whereafter reexamination showed ALT 95 u/L, AST 52 u/L and total bilirubin at 130 umol/L, with a significant decrease of liver enzyme and reduction of hepatocyte injury in a short period. If he had been treated with the original approach, it would probably have taken two months before he could be discharged from hospital.

Case 3: Ms. Zhao, female, age 32, had past positive HBsAg for 8 years, without regular treatment or periodic reexamination of relevant indicators. Over the past half year, she felt feeble, anorexic and abdominal distension after meal, but failed to give proper attention. She took orally some "stomach medicine" (specific medicine not known)

with poor effect. After the aforesaid symptoms aggravated for half a month, with urine turning as yellow as strong tea water, she was admitted to the First Affiliated Hospital of Zhengzhou University on Jan. 21, 2015. As examination upon admission showed prothrombin time activity (PTA) at 27.4%, ALT 1386 u/L, and AST 1368 u/L, she was diagnosed with acute-on-chronic liver failure, and a notice of critical illness diagnosis was given. Following active medical treatment, antiviral treatment and oral administration of TMZ, her liver function reexamination taken on February 5 showed ALT 76 u/L, AST 85 u/L, and prothrombin time activity (PTA) up to 57.8%. In merely 12 days, the patient achieved decrease of transaminase by dozens of times, relief from the critical condition, alleviated hepatocyte inflammatory responses and a favorable condition for liver cells, and greatly shortened length of hospitalization.

Case 4: Mr. Wang, male, age 52, had an operation of splenectomia because of some trauma 10 years earlier, during which he received blood transfusion. 6 years ago, physical examination detected his HBsAg was positive, but with normal liver function, and he did not take any treatment. He felt abdominal distension and nausea, accompanied with hydroncus in lower limbs, when he was tired half a month ago. For further treatment, he was admitted to the First Affiliated Hospital of Zhengzhou University on Jan. 13, 2015. Color ultrasound examination of abdomen detected diffuse changes of echo patterns of liver, cholecystolithiasis and cholecystitis. Examination showed ALT 599 u/L and AST 663 u/L. On the basis of normal hepatoprotective and antiviral treatment, he was orally administered TMZ for 13 days, whereafter reexamination showed ALT 66 u/L and AST 79 u/L. As the patient suffered from cholecystolithiasis and cholecystitis and felt abdominal pain intermittently after hospitalization, surgical evaluation suggested a cholecystectomy. The patient's liver enzyme decreased to normal level after a short period, meeting the requirements for a surgical operation. Following the operation, his abdominal pain disappeared, with liver enzyme back to normal level and improved appetite. His quality of life improves now without any discomfort.

Case 5: Mr. Shi, male, age 50, had past positive HBsAg for over 10 years, with HBsAg (+), HBeAg (+) and HBcAb (+), and had atrial fibrillation over 5 years, during which he orally took traditional Chinese medicine intermittently, but without regular treatment. He complained of feebleness, nausea, dry mouth and bitter taste, and anorexia for 6 days, and was hospitalized on Jan. 31, 2015. After admission, he had ALT 1881 u/L, AST 699 u/L, and prothrombin time activity (PTA) at 26%. The patient was extremely weak, in very poor spirits, with very poor appetite. A notice of critical illness diagnosis was given. Then he received combined treatment comprising administration of fresh refrigerated plasma, liver protection, jaundice removing, and prevention from hepatic encephalopathy, and was administered TMZ orally. One week thereafter, the reexamination of liver function showed ALT 255 u/L, AST 77 u/L, and prothrombin time activity (PTA) at 48%. His appetite and spirits improved significantly. After continued administration of TMZ for another 5 days, the reexamination of liver function showed ALT 117 u/L, AST 226 u/L, and prothrombin time activity (PTA) at 50%. The patient achieved a rapid decrease of transaminase and obvious improvement of liver synthesis function, and was safe from the critical condition. He continued to take the medicine till maturity of the treatment course, to improve the hepatocyte microcirculation and excretion of bilirubin. The patient soon recovered and left hospital.

Example 2—Large-Scale Clinical Trial

Given the efficacy of TMZ in treatment of liver failure in vitro and in vivo, we designed and registered a clinical trial to confirm the effect. We recruited totally 298 patients with liver failure according to the American and European criteria. Finally, 180 participants were included and randomized into three arms—control group, LOLA group, and TMZ treatment group (TMZ+LOLA), with 60 participants in each arm. LOLA was also included in the TMZ treatment group to meet ethical requirements. All participants were followed for 90 days and 165 participants finished the study, with 10 loss of follow-up and 5 retreat from the trial.

In this clinical trial and research involving 165 cases of liver failure (see FIG. 6), TMZ tablets (20 mg/tablet) were administered orally to the liver failure patients, one tablet each time, three times a day, over a 4-week course of treatment. As shown in the clinical trial result, compared with traditional therapeutic approach, the 30-day immortality rate of liver failure patients in the TMZ treatment group dropped from 44% to approximately 18%, and the 90-day immortality rate from 68% to 35% (see FIG. 5). This suggests that early TMZ intervention in liver failure patients can significantly increase the survival rate and improve their prognosis. No differences were found between LOLA and control groups, indicating that TMZ was responsible for the improved survival outcomes in the TMZ treatment group. The survival advantage was most significant in participants with AST or ALT lower than 400 units/L.

Figure 4:
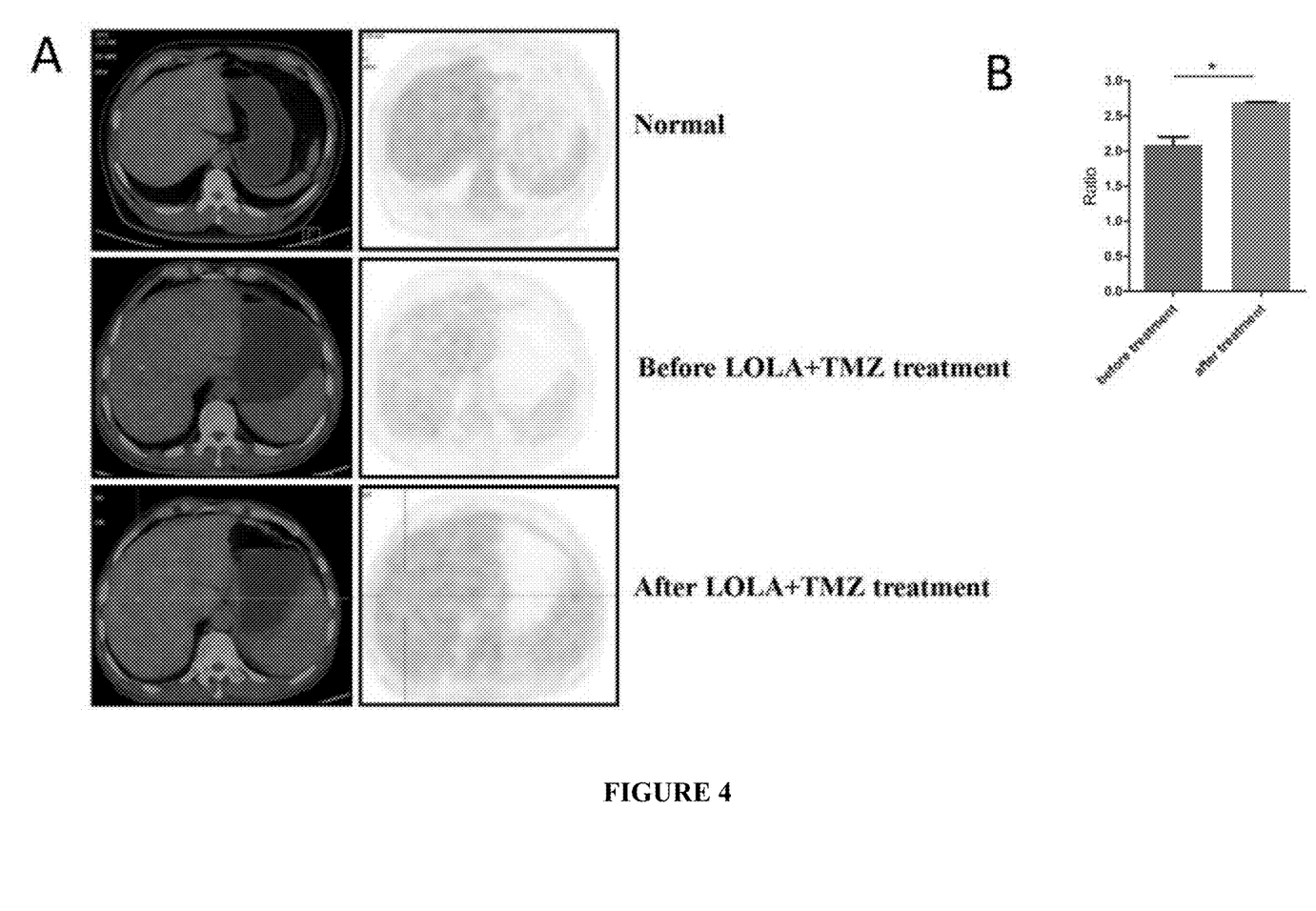
FIG. 4 shows PET-CT results of a liver failure patient before and after treatment with TMZ+LOLA. (A) Compared to normal liver, the liver of the patient had significantly reduced FDG uptake, suggesting inhibited glycolysis of hepatocytes. (B) After treatment of TMZ+LOLA, FDG uptake was increased.

Intriguingly, we were able to compare the PET-CT images before and after liver failure recovery in two participants who underwent PET-CT imaging due to suspicious liver lesions by magnet renascence imaging. Compared to normal liver and cirrhotic liver, the livers of the two participants had significantly reduced FDG uptake (FIG. 4A), suggesting inhibited glycolysis of hepatocytes. However, after treatment of TMZ+LOLA, FDG uptake was increased (FIG. 4B), suggesting the hepatic glucose metabolism of the liver failure patient was remarkably improved. This result provided further support for reduced glycolysis in liver failure and increased glycolysis after TMZ+LOLA treatment.

These clinical trial results suggests that early use of TMZ for liver failure patients can significantly improve their liver function, inhibit hepatic inflammatory response, enhance their hepatic glucose metabolism and energy utilization, and improve their chances of survival. When administered to patients suffering from liver diseases and conditions, trimetazidine is capable of providing significant hepatoprotective function, effectively decreasing transaminase (including ALT and AST), with such features as shortening the course of disease, reducing the mortality rate, easy and safe use, and low treatment cost. trimetazidine is mainly eliminated unchanged by way of urine, with the elimination half-life of approximately 6 hours, and without hepatic metabolism. Therefore, trimetazidine may cause minimal liver toxicity, while having significant hepatoprotective effect.

From liver injury rat models, Chang-liver cells treated with ammonia chloride, and the effective treatment result after administration of the medicine to the patients with clinical liver injury, it can be seen that trimetazidine is a effective drug in treatment of liver injury, and that trimetazidine can be used in treatment of acute and/or chronic liver injury induced by various viral diseases, as well as liver injury induced by various drugs or toxicants, and reduce liver injury resulting from activation of the immune system induced by unknown causes. The present invention adds a new therapeutic option for clinical treatment of liver diseases and conditions.

Example 3—In Vitro and Animal Model Study

Chang liver cells (American Type Culture Collection No. CCL-13) was cultured in RPMI1640 medium (Solarbio) containing 10% fetal bovine serum (Gibco), 100 u/mL penicillin and 100 μg/mL streptavidin, at 37° C. and under hypoxic conditions (10% $O_2$, 5% $CO_2$) and saturated humidity. The cells were exposed to 10 mM $NH_4Cl$ and treated with 1 mM LOLA, 1 mM TMZ, and 1 mM TMZ+1 mM LOLA.

Figure 7:
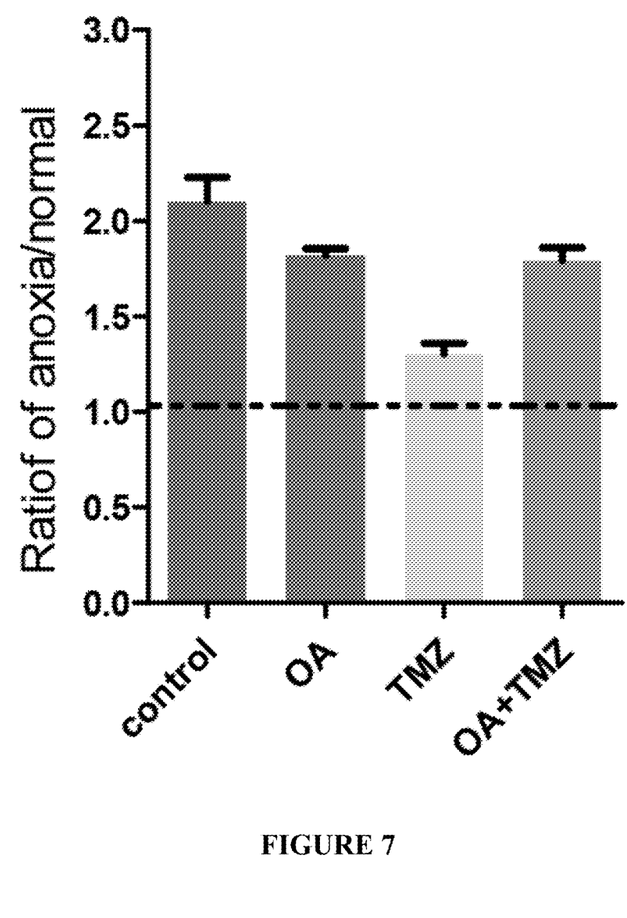
FIG. 7 shows reduction of ammonia in hepatocytes treated with LOLA, TMZ, and TMZ+LOLA. TMZ treatment exhibited greater effects compared to both LOLA treatment and TMZ+LOLA co-treatment.

FIG. 7 shows reduction of ammonia in hepatocytes treated with LOLA, TMZ, and TMZ+LOLA. TMZ treatment exhibited greater effects compared to both LOLA treatment and TMZ+LOLA co-treatment.

40 male SD rats, weighing 200±20 g, were randomly divided into five groups: saline control group (n=8), hyperammonemia group (n=8), OA (LOLA) treatment group (n=8), TMZ treatment group (n=8), and TMZ+OA co-treatment group (n=8).

Hyperammonemia group, OA group, TMZ group and TMZ+OA group were orally administered with a 10% ammonium chloride solution at 10 ml/kg body weight daily at 8:00 and 20:00. OA group received 0.8 g/kg (concentration: 0.3 g/ml) of ornithine aspartate orally; TMZ group received 0.002 g/kg (concentration: 0.00186 g/ml) of TMZ orally; TMZ+OA group received the aforementioned drugs orally at the same time point; and the saline control group received 10 ml/kg body weight of saline orally at specific time intervals. All five groups of rats were sacrificed after 30 days with pentobarbital anesthesia. Cardiac blood samples were collected to test blood levels of ammonia, ALT and AST. Liver biopsy specimens were collected and subject to hematoxylin-eosin (HE) staining and TUNEL staining to assess pathology.

Figure 8:
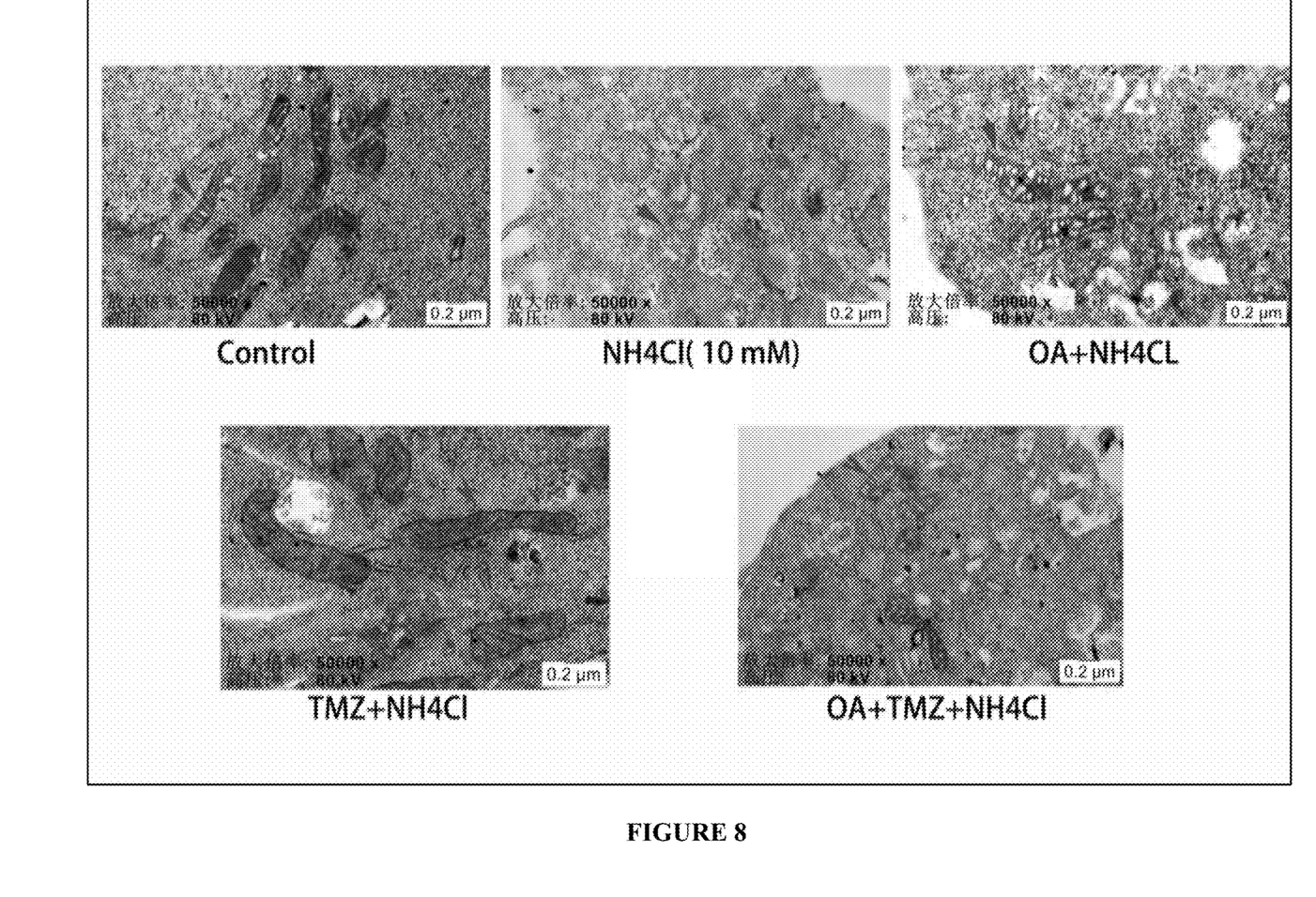
FIG. 8 shows integrity of mitochondrial structure, which is correlated with mitochondrial function. Under electronic telescope, the mitochondria in hepatocytes exposed to ammonia were commonly ruptured to different degrees, and those without rupture had vacuolar degeneration, swollen, and disordered cristal membrane. LOLA treatment decreased mitochondria rupture and swollen, but the vacuolar degeneration and cristal membrane disorder remained. TMZ+LOLA co-treatment had similar effect with LOLA treatment. TMZ treatment, however, nearly reversed the ammonia-induced mitochondria injury

FIG. 8 shows integrity of mitochondrial structure, which is correlated with mitochondrial function. Under electron microscope, the mitochondria in hepatocytes exposed to ammonia were commonly ruptured to different degrees, and those without rupture had vacuolar degeneration, swollen, and disordered cristal membrane. LOLA treatment decreased mitochondria rupture and swollen, but the vacuolar degeneration and cristal membrane disorder remained. TMZ+LOLA co-treatment had similar effect with LOLA treatment. TMZ treatment, however, nearly reversed the ammonia-induced mitochondria injury.

Figure 9:
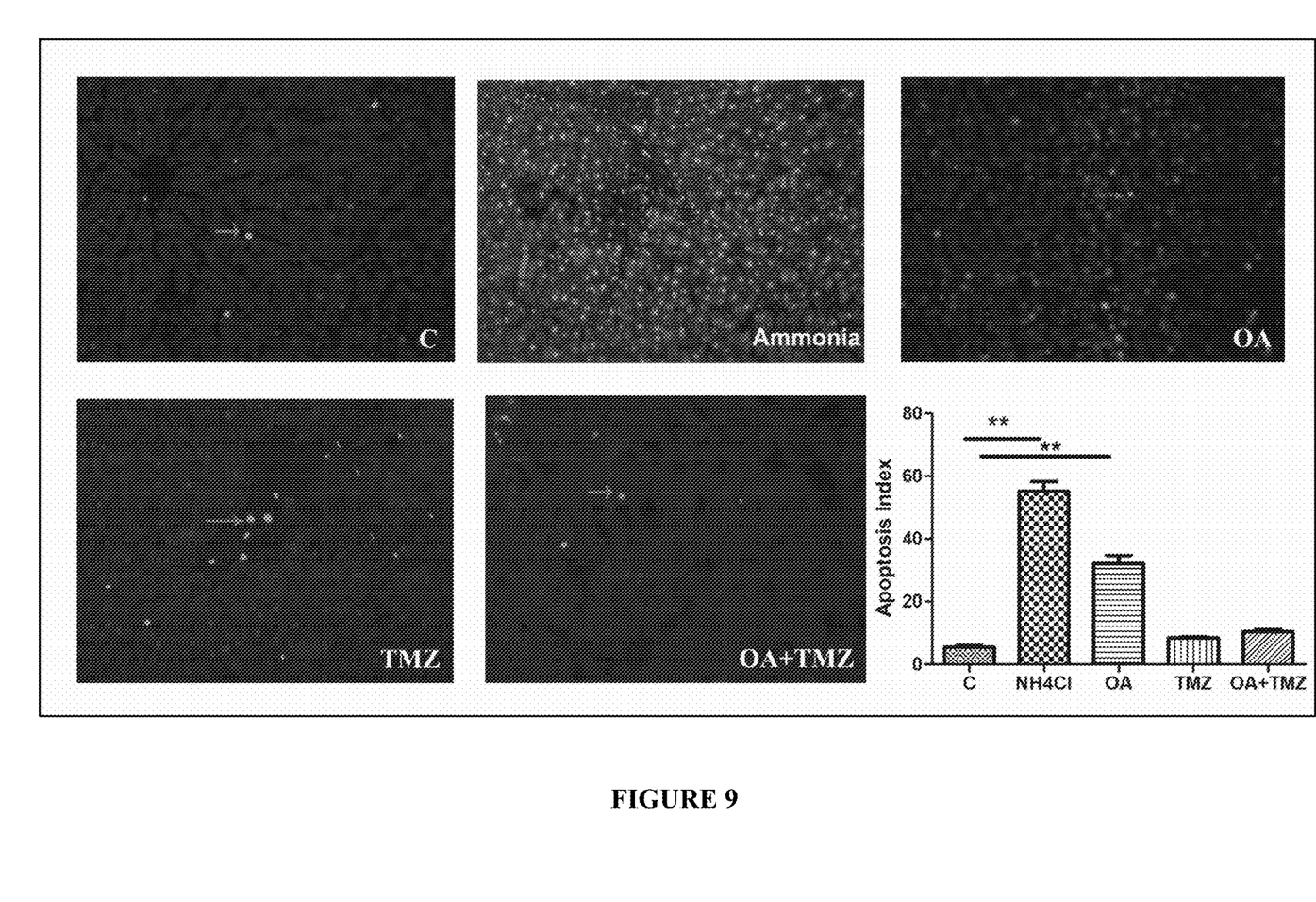
FIG. 9 shows effects of TMZ in reduction of ammonia-induced hepatocyte apoptosis. Although all four groups exposed to ammonia had increased apoptosis, TMZ treatment significantly reduced apoptosis index compared to control. TMZ treatment exhibited greater effects compared to both LOLA treatment and TMZ+LOLA co-treatment.

FIG. 9 shows effects of TMZ in reduction of ammonia-induced hepatocyte apoptosis. Although all four groups exposed to ammonia had increased apoptosis, TMZ treatment significantly reduced apoptosis index compared to control. TMZ treatment exhibited greater effects compared to both LOLA treatment and TMZ+LOLA co-treatment.

As used herein, the singular terms "a," "an," and "the" include plural referents unless the context clearly dictates otherwise.

As used herein, the terms "substantially," "substantial," and "about" are used to describe and account for small variations. When used in conjunction with an event or circumstance, the terms can refer to instances in which the event or circumstance occurs precisely as well as instances in which the event or circumstance occurs to a close approximation. For example, the terms can refer to less than or equal to ±10%, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations, which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scopes of this invention.

What is claimed is:

1. A method for treating a liver disease or condition, comprising administering to a subject suffering from a liver condition a pharmaceutical composition comprising an effective amount of trimetazidine or a pharmaceutically acceptable salt thereof as an active ingredient and wherein the liver disease or condition is acute-on-chronic liver failure.

2. The method according to claim 1, wherein the pharmaceutical composition is orally administered to the subject.

3. The method according to claim 1, wherein the pharmaceutical composition is parentally administered to the subject.

4. The method according to claim 1, wherein the pharmaceutical composition is administered to the subject 1-4 times daily.

5. The method according to claim 1, wherein the pharmaceutical composition is administered to the subject 2 or 3 times daily.

6. The method according to claim 1, wherein the subject is administered with about 30-180 mg daily of trimetazidine or a pharmaceutically acceptable salt thereof.

7. The method according to claim 1, wherein the subject is administered with about 60 mg daily of trimetazidine or a pharmaceutically acceptable salt thereof.

8. The method according to claim 1, wherein active ingredient of the pharmaceutically composition consists essentially of trimetazidine or a pharmaceutically acceptable salt thereof.

9. The method according to claim 1, wherein active ingredient of the pharmaceutically composition consists of trimetazidine or a pharmaceutically acceptable salt thereof.

10. The method according to claim 1, wherein the pharmaceutically composition further comprises a pharmaceutically acceptable carrier.

11. The method according to claim 1, wherein the subject is not suffering from angina pectoris, coronary insufficiency, old myocardial infarction, coronary heart disease, vertigo or tinnitus.

12. The method according to claim 1, wherein the pharmaceutically composition reduces activation of resting T lymphocytes to activated lymphocytes in the subject.

13. The method according to claim 1, wherein the pharmaceutically composition reduces β-oxidation in hepatocytes and reduces formation of reactive oxygen species in the subject.

14. The method according to claim 1, wherein the pharmaceutically composition reduces blood alanine aminotransferase level in the subject by at least 100 U/L after 15 days of treatment.

15. The method according to claim 1, wherein the pharmaceutically composition reduces blood aspartate transaminase level in the subject by at least 100 U/L after 15 days of treatment.

16. The method according to claim 2, wherein the pharmaceutical formulation is administered as a liquid.

17. The method according to claim 3, wherein the pharmaceutical formulation is administered intravenously.

18. The method according to claim 10, where in the effective amount of trimetazidine or a pharmaceutically acceptable salt thereof is from about 30-180 mg daily trimetazidine hydrochloride.

19. The method according to claim 18, wherein the pharmaceutical formulation is administered orally 1 to 4 times per day.

\* \* \* \* \*